United States Patent [19]

Winternitz

[11] 4,056,628
[45] Nov. 1, 1977

[54] INSECTICIDAL ESTERS OF ALPHA-PHENOXY ALKANOIC ACIDS WITH SUBSTITUTED BENZYL ALCOHOLS

[75] Inventor: Pavol Winternitz, Greifensee, Switzerland

[73] Assignee: Hoffmann-La Roche Inc., Nutley, N.J.

[21] Appl. No.: 711,330

[22] Filed: Aug. 3, 1976

[30] Foreign Application Priority Data

Aug. 8, 1975 Switzerland .................. 10380/75
June 28, 1976 Switzerland .................. 8230/76

[51] Int. Cl.$^2$ .................. A01N 9/24; C07C 69/76

[52] U.S. Cl. .................. 424/308; 424/285; 260/340.5 R; 260/347.4; 260/465 D; 560/17; 560/23; 560/43; 560/61; 560/62

[58] Field of Search .............. 260/473 G, 465 D, 470, 260/471 R, 340.5; 424/308

[56] References Cited

U.S. PATENT DOCUMENTS 3,792,082  2/1974  Nordmann et al. .............. 260/473 G Primary Examiner—Henry R. Jiles
Assistant Examiner—Bernard Dentz
Attorney, Agent, or Firm—Samuel L. Welt; Bernard S. Leon; William M. Farley

[57] ABSTRACT

Novel substituted α-aryloxycarboxylic acid esters and their preparation are described. The novel compounds are useful for the control of pests.

13 Claims, No Drawings

INSECTICIDAL ESTERS OF ALPHA-PHENOXY ALKANOIC ACIDS WITH SUBSTITUTED BENZYL ALCOHOLS

SUMMARY OF THE INVENTION

The substituted α-aryloxycarboxylic acid esters provided by the present invention have the following general formula

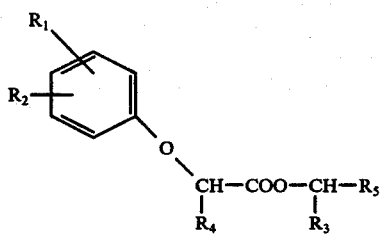

wherein $R_1$ and $R_2$ are hydrogen, halogen, alkyl containing from 1 to 3 carbon atoms, lower alkoxy, lower alkylthio, cyano or nitro; or $R_1$ and $R_2$ together are methylenedioxy; $R_3$ is hydrogen atom or cyano, lower alkenyl, lower alkynyl or lower alkyl; $R_4$ is lower alkyl group; and $R_5$ is of the formula

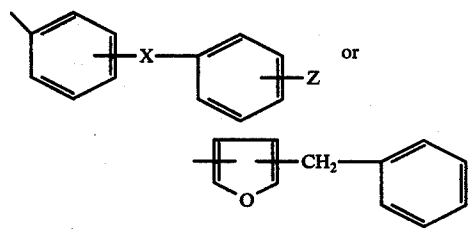

in which X is oxygen or sulphur or methylene and Z is hydrogen or fluorine.

The substituted α-aryloxycarboxylic acid esters of formula I are useful as pesticides and are especially suitable for the control of insects.

According to the process provided by the present invention, the substituted α-aryloxycarboxylic acid esters of formula I hereinbefore are prepared by a. reacting an acid of the general formula

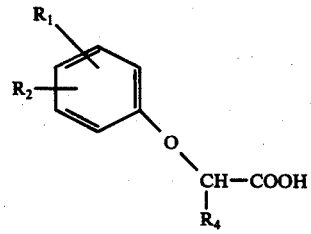

wherein $R_1$, $R_2$ and $R_4$ have the significance given earlier, or a reactive derivative thereof, with an alcohol of the general formula

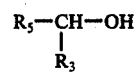

wherein $R_3$ and $R_5$ have the significance given earlier, or with a reactive derivative thereof, or b. reacting a compound of the general formula

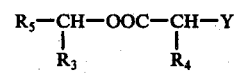

wherein $R_3$, $R_4$ and $R_5$ have the significance given earlier and Y is chlorine, bromine or iodine, with a compound of the general formula

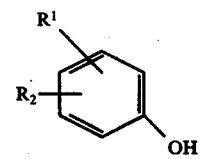

wherein $R_1$ and $R_2$ have the significance given earlier, or with an alkali metal salt thereof.

DETAILED DESCRIPTION OF THE INVENTION

As used in this specificiation, the term "lower alkyl" includes both straightchain and branched-chain hydrocarbon groups containing from 1 to 6 carbon atoms unless expressly indicated otherwise. Examples of such lower alkyl groups are methyl, ethyl, propyl, isopropyl, butyl isobutyl and tert. butyl. This definition also applies to groups which contain a lower alkyl moiety such as, for example, lower alkoxy and lower alkylthio. The term "lower alkenyl" includes straightchain and branched-chain alkenyl groups containing up to 6 carbon atoms such as the allyl, butenyl, isobutenyl, pentenyl, and isopentenyl. The term "lower alkynyl" includes straight-chain and branched-chain alkynyl groups containing up to 6 carbon atoms such as the propargyl, butynyl, isobutynyl and pentynyl. The term "halogen" means, fluorine, chlorine, bromine or iodine unless expressly indicated otherwise.

In one aspect, the present invention relates to compounds of the formula Ia

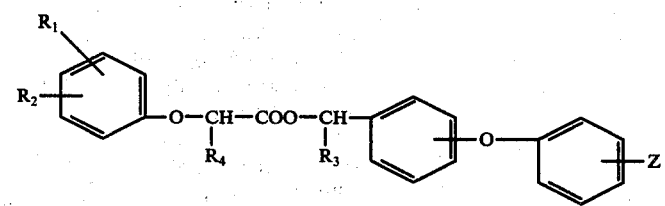

wherein $R_1$ to $R_4$ and Z have the significance given earlier.

In another aspect, the present invention relates to compounds of the formula Ib

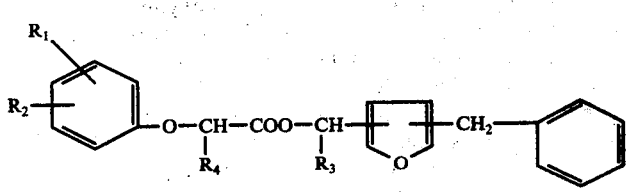

wherein $R_1$ to $R_4$ have the significance given earlier.

In still another aspect, the present invention relates to compounds of the formula Ic

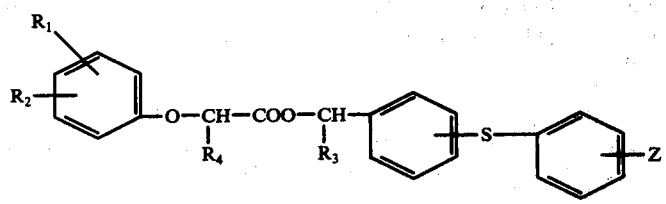

wherein $R_1$ to $R_4$ and Z have the significance given earlier.

Preferred substituted α-aryloxycarboxylic acid esters of formula I are those in which $R_1$ is lower alkyl containing from 1 to 3 carbon atoms, halogen atoms or alkoxy containing from 1 to 3 carbon atoms, $R_4$ is alkyl containing from 3 to 6 carbon atoms and $R_5$ is a group of the formula

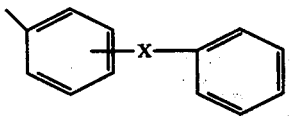

wherein X has the significance given earlier. Also preferred are substituted α-arloxycarboxylic acid esters of formula I in which $R_3$ is hydrogen, cyano or ethynyl. Of these compounds, especially preferred are those wherein $R_1$ is chlorine, methyl or methoxy and $R_4$ is alkyl containing 3 or 4 carbon atoms. Furthermore, those substituted α-aryloxycarboxylic acid esters of formula I in which $R_1$ and $R_2$ are methylenedioxy are preferred. Substituted α-aryloxycarboxylic acid esters of formula I in which $R_4$ is isopropyl are particularly preferred. Examples of such particularly preferred substituted α-aryloxycarboxylic acid esters for formula I are α-(4-tolyloxy)-isovaleric acid 3'-phenoxybenzyl ester and α-(4-chlorophenoxy)-isovaleric acid 3'-phenoxybenzyl ester.

In embodiment (a) of the present process, an acid of formula II or a reactive derivative thereof is reacted with an alcohol of formula III or with a reactive derivative thereof.

The reactive derivative of an acid of formula II can be an acid halide, an acid anhydride, an imidazolide or an ester formed with a low-boiling alcohol, an alkali metal salt, a silver salt or a salt of a tertiary amine. Halides or sulfonic acid esters are examples of reactive derivatives of alcohols of formula III.

The reaction of an acid of formula II with an alcohol of formula III in accordance with embodiment (a) of the present process is preferably carried out in a suitable inert solvent at room temperature or at an elevated temperature and under conditions suitable for the splitting off of water, for example, in the presence of dicyclohexylcarbodiimide or by azeotropically distilling off the water formed from the catalyzed reaction mixture. When an acid halide is used as the reactive derivative of an acid of formula II, the reaction with an alcohol of formula III is carried out at room temperature and in the presence of an acid acceptor (e.g., a tertiary amine such as pyridine or triethylamine). The corresponding ester of formula I is obtained in a high yield. Acid hlorides are the preferred acid halides. The reaction is preferably carried out in the presence of an inert solvent such as benzene, toluene or petroleum ether. When an ester formed with a low-boiling alcohol (e.g., methnaol or ethanol) is used as the reactive derivative of an acid of formula II, the corresponding acetic acid ester of formula I can be prepared in a high yield by heating the ester with an alcohol of formula III in the presence of a base, preferably with an alkali metal alcoholate corresponding to the low-boiling alcohol of the ester used, or in the presence of sodium hydride in an inert solvent (e.g., toluene) and separating off by fractional distillation the low-boiling alcohol liberated during the reaction.

The substituted α-aryloxycarboxylic acid esters of formula I can be prepared in a good yield by reacting the imidazolide of an acid of formula II with an alkali metal alcoholate derived from an alcohol of formula III or with an alcohol of formula III together with a catalytic amount of an alkali metal alcoholate. The reaction is preferably carried out in an inert solvent such as tetrahydrofuran or dimethoxyethane at room temperature.

When an acid anhydride is used as the reactive derivative of an acid of formula II, an acetic acid ester of formula I can be manufactured by reacting the acid anhydride with an alcohol of formula III at room temperature or, preferably, at an elevated temperature, and in the presence of a solvent such as toluene of xylene. When a halide or sulfonic acid ester of an alcohol of formula III is used, an acid of formula II is generally used in the form of an alkali metal salt, the silver salt or a salt with a tertiary amine. These salts can be prepared in situ by adding the corresponding base to an acid of formula II. In this case, a solvent such as benzene, acetone or dimethylformamide is preferably used and the reaction is preferably carried out while heating the reaction mixture to the boiling point or below the boiling point of the solvent used. The preferred halides of the alcohols of formula III are the chlorides and bromides.

In embodiment (b) of the present process, a compound of formula IV is reacted with a compound of formula V or with an alkali metal salt thereof in a manner known per se. The reaction is conveniently carried out in an inert organic solvent such as a hydrocarbon (e.g., benzene or toluene), an ether (e.g., diethyl ether, tetrahydrofuran or dimethoxyethane), a ketone (e.g., acetone), hexamethylphosphoric acid triamide or the like. The temperature and pressure are not critical, the reaction being preferably carried out at a temperature between about $-20°$ C. and the reflux temperature of the reaction mixture, preberably at between $-10°$ C. and $30°$ C.

It will be appreciated that formula I hereinbefore embraces not only racemates but also optical isomers since one asymmetric carbon atom is present in the $\alpha$-position to the carboxyl and another asymmetric carbon atom may be present in the ester group when $R_3$ is other than hydrogen.

Certain of the starting materials of formula II are novel. The can be prepared by reacting a compound of formula V with a compound of the general formula

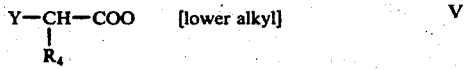

wherein $R_4$ and Y have the significance given earlier. This reaction is carried out under the same conditions as described earlier in connection with the reaction of a compound of formula IV with a compound of formula V. The resulting ester is saponified in a manner known per se and the resulting acid of formula II can then be converted in a customary manner into a reactive derivative.

Certain of the starting materials of formula IV are also novel. They can be prepared by reacting an acid of the general formula

wherein $R_4$ and Y have the significance given earlier, or a reactive derivative thereof, with an alcohol of formula III. This reaction can be carried out according to any customary esterification method in which no bases are used.

The present invention is also concerned with pesticidal compositions which contain as essential active ingredient or essential active ingredients one or more of the substituted $\alpha$-aryloxycarboxylic acid esters of formula I in association with a compatible carrier material. The pesticidal compositions conveniently contain at least one of the following materials: carrier substances, wetting agents, inert diluents and solvents.

Further, the present invention is concerned with a method of combatting pests which method comprises applying to a material to be protected a pesticidal composition as hereinbefore defined. The material can be, for example, plants, animals, soil objects and areas.

The substituted $\alpha$-aryloxycarboxylic acid esters for formula I are accordingly of value as pesticides. They are particularly valuable as insecticides, in particular against flies, caterpillars, beetles and aphids. They are effective as direct insecticides and some of them also have a systemic activity. Furthermore, they are of value in the control of pests in animals. Thus, for example, $\alpha$-(4-tolyloxy)isovaleric acid 3'-phenoxybenzyl ester shows an activity of 100% in a concentration of $10^{-7}$ g/cm$^2$ in the test against Spodoptera littoralis in the first larval stage and an activity of 41% in a concentration of $10^{-6}$ g/cm$^2$ in the curative test against Aphis fabae. Further, $\alpha$-(4-chlorophenoxy)-isovaleric acid $\alpha$-ethynyl-3'-phenoxybenzyl ester shows an activity of 56% in a concentration of $10^{-7}$ g/cm$^2$ in the test against mobile states of Tetranicus urticae.

The substituted $\alpha$-aryloxycarboxylic acid esters of formula I are active, for example, against the insects and representatives of the order Acarina listed hereinafter:

| | |
|---|---|
| Diptera | Aedes aegypti |
| | Ceratitis capitata |
| | Culex pipiens |
| | Musca domestica |
| | Anopheles stephensi |
| Lepidoptera | Adoxophyes reticulana |
| | Ephestia kuhniella |
| | Heliothis virescens |
| | Laspeyresia pomonella |
| | Ostrinia nubilalis |
| | Plodia interpunctella |
| | Spodoptera littoralis |
| Homoptera | Aphis fabae |
| | Aphis pomi |
| | Aonidiella aurantii |
| | Quadraspidiotus perniciosus |
| | Laodelphax striatellus |
| | Nephotettix virescens |
| | Coccus hesperidum |
| | Saissetia coffeae |
| | Myzus persicae |
| | Planococcus citri |
| | Dysaphis plantaginea |
| Heteroptera | Dysdercus cingulatus |
| Aleyrodidae | Trialeurodes vaporariorum |
| Thysanoptera | Thrips tabaci |
| Coleoptera | Anthonomus grandis |
| | Epilanchna chrysomelina |
| | Leptinotarsa decemlineata |
| | Rhizopertha dominica |
| | Sitophilus granarius |
| Orthoptera | Blatella germanica |
| Arachnida | Tetranychus urticae |
| Acarina | Tetranychus cinnabarinus |
| | Panonychus ulmi |

The substituted $\alpha$-aryloxycarboxylic acid esters of formula I are, in general, insoluble in water and can be made into a ready-for-use form according to any method which is customarily used for the formulation of water-insoluble compounds.

If desired, the substituted $\alpha$-aryloxycarboxylic acid esters of formula I can be dissolved in a water-immiscible solvent such as, for example, a high boiling hydrocarbon, which conveniently contains dissolved emulsifiers, so that it acts as a self-emulsifiable oil upon addition to water.

The substituted $\alpha$-aryloxycarboxylic acid esters of formula I can also be mixed with a wetting agent, with or without an inert diluent, to form a wettable powder which is soluble or dispersible in water, or they can be mixed with inert diluents to form a solid or pulverous product.

Inert diluents with which the substituted $\alpha$-arloxycarboxylic acid esters of formula I can be processed are solid inert media, including pulverous or finely divided solid materials such as, for example, clays, sands, talcs, mica, fertilizers and the like. The resulting compositions can be present either in the form of dusts or as materials having a larger particle size.

The wetting agent referred to earlier can be an anionic compound such as, for example, soaps, fatty sulphate esters such as dodecyl sodium sulphate, octadecyl sodium sulphate and cetyl sodium sulfphate, fatty-aromatic sulphonates such as alkylbenzene sulphonates or butylnaphthalene sulfonates, complex fatty sulphonates such as the amide condensation product of oleic acid and N-methyltaurin or the sodium sulphonate of dioctyl succinate.

The wetting agent can also be a non-ionic wetting agent such as, for example, condensation products of fatty acids, fatty alcohols or fat-substituted phenols with ethylene oxide, or fatty acid esters and ethers of sugars or polyvalent alcohols or the product which are obtained from the latter by condensation with ethylene oxide, or the products which are known as block copolymers of ethylene oxide and propylene oxide.

The wetting agent can also be cationic agent such as, for example, cetyltrimethylammonium bromide and the like.

The pesticidal compositions can also be present in the form of an aerosol, there being conveniently used in addition to the propellant gas, which is suitably a polyhalogenated alkane such as dichlorodifluoromethane, a co-solvent and a wetting agent.

The pesticidal compositions provided by the present invention can contain, in addition, to one or more of the substituted α-aryloxycarboxylic acid esters of formula I, synergistic and other active insecticides, bactericides and fungicides.

In their various fields of application, the substituted α-aryloxycarboxylic acid esters of formula I can be applied in varying amounts. Thus, for example, for the treatment of plants for the control of pests thereon, the present substituted α-arloxycarboxylic acid esters are conveniently applied in an amount of about 4–400 g. per acre and for the treatment of animals for the control of ectoparasites thereon, the animal is conveniently dipped in a solution containing 10–500 parts per million of substituted α-aryloxycarboxylic acid ester or sprayed with such a solution.

The following Example illustrate the process provided by the present invention. All the compounds are racemates unless otherwise indicated.

EXAMPLE 1

1.04 G. (0.005 mol) of α-(4-tolyloxy)-isovaleric acid are held under reflux for 2 hours with 3.54 g. (0.03 mol) of freshly distilled thionyl chloride in 5 ml. of hexane and the mixture is then evaporated to dryness in vacuo with the exclusion of moisture. The resulting acid chloride is dissolved in 20 ml. of anhydrous benzene and cooled to 0° C. The mixture is treated with a solution of 1.00 g. (0.005 mol) of 3-phenoxybenzyl alcohol and 2.37 g. (0.03 mol) of anhydrous pyridine in 10 ml. of benzene and the resulting mixture is stirred for 30 minutes at room temperature. The mixture is then diluted with 100 ml. of ether and shaken out with three 100 ml. portions of water, dried over sodium sulphate and evaporated to dryness under reduced pressure. The crude product is purified by chromatography on silica gel using ethyl acetate/hexane (1:6) for the elution. There is thus obtained α-(4-tolyloxy)-isovaleric acid 3'-phenoxybenzyl ester as a viscous oil; $n_D^{30} = 1.5585$.

EXAMPLE 2

13.0 G. (0.1 mol) of anhydrous sodium p-cresolate are suspended in 70 ml. of hexamethylphosphoric acid triamide whilst stirring and treated over a period of 4 hours at −10° C. with a solution of 20.9 g. (0.1 mol) of α-bromo-isovaleric acid ethyl ester in 50 ml. of hexamethylphosphoric acid triamide. The mixture is stirred for 15 hours at −10° C. and then for 2 hours at room temperature, poured into 2 liters of water and treated with a small amount of sodium chloride. The mixture is shaken out with three 100 ml. portions of ether, the ether phases are washed with water, dried over sodium sulphate and evaporated to dryness under reduced pressure. The liquid residue is pre-purified by chromatography on aluminium oxide using ethyl acetate/hexane (1:19) for the elution and then fractionated using a Widmer column. There is obtained [α-(4-tolyloxy)isovaleric acid] ethyl ester of boiling point 72°–76° C./0.02 mm. Hg.

EXAMPLE 3

7.0 G. (0.03 mol) of ethyl ester of Example 3 are dissolved in 100 ml. of ethanol and held under reflux for 5 hours with a solution of 12.0 g. (0.3 mol) of sodium hydroxide in 50 ml. of water. The ethanol is distilled off under reduced pressure, the residue is treated with 100 ml. of water and a small amount of sodium chloride and then shaken out with three 100 ml. portions of ether. The aqueous phase is acidified with dilute sulphuric acid and again shaken out with three 100 ml. portions of ether. The extracts are washed neutral, dried over sodium sulphate and evaporated to dryness. There is thus obtained the desired acid in the form of colorless crystals of melting point 75°–77° C. (from hexane).

EXAMPLE 4

1.04 G. (0.005 mol) of α-(4-tolyloxy)-isovaleric acid dissolved in 2 ml. of anhydrous tetrahydrofuran are added at room temperature and while stirring to a suspension of 0.85 g. (0.00525 mol) of N,N'-carbonyl-diimidazole in 5 ml. of tetrahydrofuran. After the formation of carbon dioxide has ended, the yellow imidazolide solution is treated with an alcoholate suspension prepared from 1.00 g. (0.005 mol) of 3-phenoxybenzyl alcohol and 0.115 g. (0.005 gram atom) of sodium in 5 ml. of tetrahydrofuran and the mixture is stirred for 1 hour at room temperature. The mixture is then diluted with 100 ml. of ether, washed with three 100 ml. portions of water, dired over sodium sulphate and evaporated to dryness under reduced pressure. The crude product is purified by chromatography on silica gel using ethyl acetate/hexane (1:5) for the elution. There is obtained α-(4-tolyloxy)-isovaleric acid 3'-phenoxybenzyl ester as a viscous light-colored oil; $n_D^{30} = 1.5585$.

EXAMPLE 5

The procedure described in Example 1 is repeated using an equivalent amount of α-(3-tolyloxy)-isovaleric aicd in the place of the α-(4-tolyloxy)-isovaleric acid. There is obtained α-(3-tolyloxy)-isovaleric acid 3'-phenoxybenzyl ester as a light-colored viscous oil; $n_D^{30} = 1.5600$.

EXAMPLE 6

α-(3-tolyloxy)-isovaleric acid having a melting point of 58°–60° C. is prepared via α-(3-tolyloxy)-isovaleric acid ethyl ester (boiling point 67°–68° C./0.01 mm. Hg.)

in analogy to the procedure described in Examples 2 and 3.

EXAMPLE 7

The procedure described in Example 1 is repeated using an equivalent amount of α-(2-tolyloxy)-isovaleric acid in place of the α-(4-tolyloxy)-isovaleric acid. There is obtained α-(2-tolyloxy)-isovaleric acid 3'-phenoxybenzyl ester as a light-colored viscous oil; $n_D^{30}$ = 1.5587.

EXAMPLE 8

α-(2-tolyloxy)-isovaleric acid having a melting point of 83°–85° C. is prepared via α-(2-tolyloxy)-isovaleric acid ethyl ester (boiling point of 68°–70° C./0.01 mm. Hg.) in analogy to the procedure described in Example 2 and 3.

EXAMPLE 9

The procedures described in Example 1 is repeated using an equivalent amount of α-(3,5-xylyloxy)-isovaleric acid in place of the α-(4-tolyloxy)isovaleric acid. There is obtained α-(3,5-xylyloxy)-isovaleric acid 3'-phenoxybenzyl ester as a light-colored viscous oil; $n_D^{30}$ = 1.5563.

EXAMPLE 10

α-(3,5-xylyloxy)-isovaleric acid having a melting point of 64°–66° C. is prepared via α-(3,5-xylyloxy)-isovaleric acid ethyl ester (boiling point of 70°–72° C./0.01 mm. Hg.) in analogy to the procedure described in Examples 2 and 3.

EXAMPLE 11

The procedure described in Example 1 is repeated using an equivalent amount of α-(3,4-xylyloxy)-isovaleric acid in place of the α-(4-tolyloxy)-isovaleric acid. There is obtained α-(3,4-xyloxy)-isovaleric acid 3'-phenoxybenzyl ester as a light-colored viscous oil; $n_D^{30}$ = 1.5587.

EXAMPLE 12

α-(3,4-xylyloxy)-isovaleric acid, a viscous oil, is prepared via α-(3,4-xylyloxy)-isovaleric acid ethyl ester (boiling point of 83°–86° C./0.015 mm. Hg.) is analogy to the procedure described in Examples 2 and 3.

EXAMPLE 13

The procedure described in Example 1 is repeated using an equivalent amount of α-(2,4-xylyloxy)-isovaleric acid in place of the α-(4-tolyloxy)-isovaleric acid. There is obtained α-(2,4-xylyloxy)-isovaleric acid 3'-phenoxybenzyl ester as a light colored viscous oil; $n_D^{30}$ = 1.5553.

EXAMPLE 14

α-(2,4-xylyloxy)-isovaleric acid, a viscous oil is prepared via α-(2,4-xylyloxy)-isovaleric acid ethyl ester (boiling point of 80°–82° C./0.02 mm. Hg.) in analogy to the procedure described in Examples 2 and 3.

EXAMPLE 15

The procedure described in Example 1 is repeated using an equivalent amount of α-(4-chlorophenoxy)-isovaleric acid in place of the α-(4-tolyloxy)-isovaleric acid. There is obtained α-(4-chlorophenoxy)-isovaleric acid 3'-phenoxybenzyl ester as a light-colored viscous oil; $n_D^{30}$ = 1.5654.

EXAMPLE 16

The α-(4-chlorophenoxy)-isovaleric acid has a melting point of 88°–91° C. and the α-(4-chlorophenoxy)-isovaleric acid ethyl ester obtained in the preparation thereof has a boiling point of 72°–75° C./0.02 mm. Hg.

EXAMPLE 17

The procedures described in Example 1 is repeated using an equivalent amount of α-(4-ethylphenoxy)-isovaleric acid in place of the α-(4-tolyloxy)-isovaleric acid. There is obtained α-(4-ethylphenoxy)-isovaleric acid 3'-phenoxybenzyl ester as a light-colored viscous oil; $n_D^{30}$ = 1.5551.

EXAMPLE 18

α-(4-ethylphenoxy)-isovaleric acid, a viscous oil is prepared via α-(4-ethylphenoxy)-isovaleric acid ethyl ester (boiling point of 74°–79° C./0.02mm. Hg.) in analogy to the procedure described in Example 1 and 3.

EXAMPLE 19

The procedure described in Example 1 is repeated using an equivalent amount of α-(4-isopropylphenoxy)-isovaleric acid in the place of the α(4-tolyloxy)-isovaleric acid. There is obtained α-(4-isopropylphenoxy)-isovaleric aicd 3'-phenoxybenzyl ester as a light-colored viscous oil; $n_D^{30}$ = 1.5501.

EXAMPLE 20

α-(4-isopropylphenoxy)-isovaleric acid, a viscous oil, is prepared via α-(4-isopropylphenoxy)-isovaleric acid ethyl ester (boiling point of 83°–84° C./0.02 mm. Hg. ) in analogy to the procedure described in Example 2 and 3.

EXAMPLE 21

The procedure described in Example 1 is repeated using an equivalent amount of α-(4-methoxyphenoxy)-isovaleric acid in place of the α-(4-tolyloxy)-isovaleric acid. There is obtained α-(4-methoxyphenoxy)-isovaleric acid 3'-phenoxybenzyl ester as a light-colored viscous oil; $n_D^{30}$ = 1.5596.

EXAMPLE 22

α-(4-methoxyphenoxy)-isovaleric acid having a melting point of 65°–67° C. is prepared via α-(4-methoxyphenoxy)-isovaleric acid ethyl ester (boiling point of 83°–86° C./0.02 mm. Hg.) in analogy to the procedure described in Examples 2 and 3.

EXAMPLE 23

The procedure described in Example 1 is repeated using an equivalent amount of α-(4-bromophenoxy)-isovaleric acid in place of the α-(4-tolyloxy)-isovaleric acid. There is obtained α-(4-bromophenoxy)-isovaleric acid 3'-phenoxybenzyl ester as a light-colored viscous oil; $n_D^{30}$ = 1.5756.

EXAMPLE 24

α-(4-bromophenoxy)-isovaleric acid having a melting point of 102°–104° C. is prepared via α-(4-bromophenoxy)-isovaleric acid ethyl ester (boiling point of 84°–86° C./0.025 mm. Hg.) in analogy to the procedure described in Examples 2 and 3.

EXAMPLE 25

The procedure described in Example 4 is repeated using an equivalent amount of α-(3,4-methylenedioxyphenoxy)-isovaleric acid in place of the α-(4-tolyloxy)-isovaleric acid. There is obtained α-(3,4-methylenedioxyphenoxy)-isovaleric acid 3'-phenoxybenzyl ester as a light colored viscous oil; $n_D^{30} = 1.5677$.

EXAMPLE 26

α-(3,4-methylenedioxyphenoxy)-isovaleric acid, a viscous oil, is prepared via α-(3,4-methylenedioxyphenoxy)-isovaleric acid ethyl ester (boiling point of 105°–107° C./0.02 mm. Hg.) in analogy to the procedure described in Examples 2 and 3.

EXAMPLE 27

The procedure described in Exaple 4 is repeated using an equivalent amount of α-(4-methylthiophenoxy)-isovaleric acid in place of the α-(4-tolyloxy)-isovaleric acid. There is obtained α-(4-methylthiophenoxy)-isovaleric acid 3'-phenoxybenzyl ester as a light-colored viscous oil; $n_D^{30} = 1.5813$.

EXAMPLE 28

α-(4-methylthiophenoxy)-isovaleric acid having a melting point of 77°–80° C. is prepared via α-(4-methylthiophenoxy)-isovaleric acid ethyl ester (boiling point of 102°–105° C./0.02 mm. Hg.) in analogy to the procedure described in Examples 2 and 3.

EXAMPLE 29

The procedure described in Example 4 is repeated using an equivalent amount of α-(4-cyanophenoxy)-isovaleric acid in place of the α-(4-tolyloxy)-isovaleric acid. There is obtained α-(4-cyanophenoxy)-isovaleric acid 3'-phenoxybenzyl ester as a light colored viscous oil; $n_D^{30} = 2.5706$.

EXAMPLE 30

α-(4-cyanophenoxy)-isovaleric acid having a melting point of 93°–95° C. is prepared via α-(4-cyanophenoxy)-isovaleric acid ethyl ester (boiling point of 106°–108° C./0.02 mm. Hg.) in analogy to the procedure described in Examples 2 and 3.

EXAMPLE 31

The procedure described in Example 4 is repeated using an equivalent amount of α-(4-nitrophenoxy)-Isovaleric acid in place of the α-(4-tolyloxy)-isovaleric acid. There is obtained α-(4-nitrophenoxy)-isovaleric acid 3'-phenoxybenzyl ester as a light-colored viscous oil; $n_D^{30} = 1.5781$.

EXAMPLE 32

2-(4-nitrophenoxy)-isovaleric acid having a melting point of 125°–128° C. is prepared via α-(4-nitrophenoxy)-isovaleric acid ethyl ester (boiling point of 117°–120° C./0.02 mm. Hg.) in analogy to the procedure described in Examples 2 and 3.

EXAMPLE 33

The procedure described in Example 1 is repeated using an equivalent amount of α-phenoxyisovaleric acid in place of the α-(4-tolyloxy)-isovaleric acid. There is obtained α-phenoxy-isovaleric acid 3'-phenoxybenzyl ester as a light-colored viscous oil; $n_D^{30} = 1.5618$.

EXAMPLE 34

α-phenoxyisovaleric acid having a melting point of 74°–77° C. is prepared via α-phenoxyisovaleric acid ethyl ester (boiling point of 54°–56° C. /0.02 mm. Hg.) in analogy to the procedure described in Examples 2 and 3.

EXAMPLE 35

The procedure described in Example 1 is repeated using α-(4-chlorophenoxy)- isovaleric acid as the acid component and 5-benzyl-3-furylmethanol as the alcohol component. There is obtained α-(4-chlorophenoxy)-isovaleric acid 5'-benzyl-3'- furylmethyl ester as a pale yellow viscous oil; $n_D^{30}$ 1.5484.

EXAMPLE 36

The procedure described in Example 1 is repeated using α-(4-methoxyphenoxy)-isovaleric acid as the acid component and 5-benzyl-3-furylmethanol as the alcohol component. There is obtained α-(4-methoxyphenoxy)-isovaleric acid 5'-benzyl-3'-furylmethyl ester as a pale yellow viscous oil; $n_D^{30} = 1.5439$.

EXAMPLE 37

The procedure described in Example 1 is repeated using 5-benzyl-3-furylmethanol as the alcohol component. There is obtained α-(4-tolyloxy)-isovaleric acid 5'-benzyl-3'-furylmethyl ester as a pale yellow viscous oil; $n_D^{30} = 1.5401$.

EXAMPLE 38

The procedure described in Example 1 is repeated using an equivalent amount of α-(4-tert.butylphenoxy)-isovaleric acid in place of the α-(4-tolyloxy)-isovaleric acid. There is obtained α-(4-tert.butylphenoxy)-isovaleric acid 3'-phenoxybenzyl ester as a pale yellow viscous oil; $n_D^{30} = 1.5489$.

EXAMPLE 39

α-(4-tert.butylphenoxy)-isovaleric acid having a melting point of 48°–53° C. is prepared via α-(4-tert. butylphenoxy)-isovaleric acid ethyl ester (boiling point of 87°–88° C. /0.02 mm. Hg.) in analogy to the procedure described in Examples 2 and 3.

EXAMPLE 40

The procedure described in Example 1 is repeated using an equivalent amount of α-(3-bromophenoxy)-isovaleric acid in place of the α-(4-tolyloxy)-isovaleric acid. There is obtained α-(3 -bromophenoxy)-isovaleric acid 3'-phenoxybenzyl ester as a pale yellow viscous oil; $n_D^{30} = 1.5753$.

EXAMPLE 41

α-(3-bromophenoxy)-isovaleric acid having a melting point of 58°–60° C. is prepared via α-(3-bromophenoxy)-isovaleric acid ethyl ester (boiling point of 84°–85° C. /0.02 mm. Hg.) in analogy to the procedure described in Examples 2 and 3.

EXAMPLE 42

The procedure described in Example 1 is repeated using an equivalent amount of α-(4-ethoxyphenoxy)-isovaleric acid in place of the α-(4-tolyloxy-isovaleric acid. There is obtained α-(4-ethoxyphenoxy)-isovaleric acid 3'-phenoxybenzyl ester as a pale yellow viscous oil; $n_D^{30} = 1.5591$.

EXAMPLE 43

α-(4-ethoxyphenoxy)-isovaleric acid having a melting point of 59°–61° C. is prepared via α-(4-ethoxyphenoxy)-isovaleric acid ethyl ester (boiling point of 90°–92° C./0.02 mm. Hg.) in analogy to the procedure described in Examples 2 and 3.

EXAMPLE 44

The procedure described in Example 1 is repeated using an equivalent amount of α-(3-methoxyphenoxy)-isovaleric acid in place of the α-(4-tolyloxy)-isovaleric acid. There is obtained α-(3-methoxyphenoxy)-isovaleric acid 3'-phenoxybenzyl ester as a light-colored viscous oil; $n_D^{30}$ = 1.5632.

EXAMPLE 45

α-(3-methoxyphenoxy)-isovaleric acid, a viscous oil, is prepared via α-(3-methoxyephnoxy)-isovaleric acid ethyl ester (boiling point of 92°–95° C./0.02 mm. Hg.) in analogy to the procedure described in Examples 2 and 3.

EXAMPLE 46

The procedure described in Example 1 is repeated using α-cyano-3-phenoxybenzyl alcohol as the alcohol component. There is obtained α-(4-tolyloxy)-isovaleric acid α'-cyano-3'-phenoxybenzyl ester as a pale yellow oil; $n_D^{30}$ = 1.5543.

EXAMPLE 47

The procedure described in Example 1 is repeated using α-(4-methoxyphenoxy)-isovaleric acid as the acid component and α-cyano-3-phenoxybenzyl alcohol as the alcohol component. There is obtained α-(4-methoxyphenoxy)-isovaleric acid α'-cyano-3'-phenoxybenzyl ester as a pale yellow oil; $n_D^{30}$ = 1.5582.

EXAMPLE 48

The procedure described in Example 1 is repeated using an equivalent amount of α-(4-chloro-2-methylphenoxy)-isovaleric acid in place of the α-(4-tolyloxy)-isovaleric acid. There is obtained α-(4-chloro-2-methylphenoxy)-isovaleric acid 3'-phenoxybenzyl ester as a light-colored viscous oil; $n_D^{30}$ = 1.5619.

EXAMPLE 49

α-(4-chloro-2-methylphenoxy)-isovaleric acid having a melting point of 84°–86° C. is prepared via α-(4-chloro-2-methylphenoxy)-isovaleric acid ethyl ester (boiling point 82°–85° C./0.02 mm. Hg.) in analogy to the procedure described in Examples 2 and 3.

EXAMPLE 50

The procedure described in Example 1 is repeated using an equivalent amount of α-(6-isopropyl-3-methylphenoxy)-isovaleric acid in place of the α-(4-tolyloxy)-isovaleric acid. There is obtained α-(6-isopropyl-3-methylphenoxy)-isovaleric acid 3'-phenoxybenzyl ester as a light-colored viscous oil; $n_D^{30}$ = 1.5497.

EXAMPLE 51

α-(6-isopropyl-3-methylphenoxy)-isovaleric acid, a viscous oil, is prepared via α-(6-isopropyl-3-methylphenoxy)-isovaleric acid ethyl ester (boiling point of 85°–88° C./0.04 mm. Hg.) in analogy to the procedure described in Examples 2 and 3.

EXAMPLE 52

The procedure described in Example 1 is repeated using an equivalent amount of α-(5-isopropyl-2-methylphenoxy)-isovaleric acid in place of the α-(4-tolyloxy)-isovaleric acid. There is obtained α-(5-isopropyl-2-methylphenoxy)-isovaleric acid 3'-phenoxybenzyl ester as a light-colored viscous oil; $n_D^{30}$ = 1.5468.

EXAMPLE 53

α-(5-isopropyl-2-methylphenoxy)-isovaleric acid, a viscous oil, is prepared via α-(5-isopropyl-2-methylphenoxy)-isovaleric acid ethyl ester (boiling point of 83°–84° C./0.03 mm. Hg.) in analogy to the procedure described in Examples 2 and 3.

EXAMPLE 54

The procedure described in Example 1 is repeated using an equivalent amount of α-(2,4-dichlorophenoxy)-isovaleric acid in place of the α-(4-tolyloxy)-isovaleric acid. There is obtained α-(2,4-dichlorophenoxy)-isovaleric acid 3'-phenoxybenzyl ester as a light-colored viscous oil; $n_D^{30}$ = 1.5713.

EXAMPLE 55

α-(2,4-dichlorophenoxy)-isovaleric acid having a melting point of 61°–63° C. is prepared via α-(2,4-dichlorophenoxy)-isovaleric acid ethyl ester (boiling point of 95°–99° C./0.02 mm. Hg.) in analogy to the procedure described in Examples 2 and 3.

EXAMPLE 56

The procedure described in Example 1 is repeated using α-ethynyl-3-penoxybenzyl alcohol as the alcohol component. There is obtained α-(4-tolyloxy)-isovaleric acid α'-ehtynyl-3'-phenoxybenzyl ester as a pale yellow oil; $n_D^{30}$ = 1.5609.

EXAMPLE 57

The procedure described in Example 1 is repeated using α-(4-methoxyphenoxy)-isovaleric acid as the acid component and α-ethynyl-3-phenoxybenzyl alcohol as the alcohol component. There is obtained α-(4-methoxyphenoxy)-isovaleric acid α'-ethynyl-3'-phenoxybenzyl ester as a light-colored oil; $n_D^{30}$ = 1.5609.

EXAMPLE 58

The procedure described in Example 1 is repeated using α-(4-chlorophenoxy)-isovaleric acid as the acid component and α-ethynyl-3-pehnoxybenzyl alcohol as the alcohol component. There is obtained α-(4-chlorophenoxy)-isovaleric acid α'-ethynyl-3'-phenoxybenzyl ester as a light-colored viscous oil; $n_D^{30}$ = 1.5678.

EXAMPLE 59

The procedure described in Example 1 is repeated using α-tert.butyl-3-phenoxybenzyl alcohol as the alcohol component. There is obtained α-(4-tolyloxy)-isovaleric acid α'-tert.butyl-3'-phenoxybenzyl ester as a light-colored viscous oil; $n_D^{30}$ = 1.5450.

EXAMPLE 60

The procedure described in Example 1 is repeated using α-(4-chlorophenoxy)-isovaleric acid as the acid component and α-tert.butyl-3-phenoxy-benzyl alcohol as the alcohol component. There is obtained α-(4-chlorophenoxy)-isovaleric acid α'-tert.butyl-3'-phenoxybenzyl ester as a light-colored viscous oil; $n_D^{30}$ = 1.5513.

EXAMPLE 61

The procedure described in Example 1 is repeated using α-allyl-3-phenoxybenzyl alcohol as the alcohol component. There is obtained α-(4-tolyloxy)-isovaleric acid α'-allyl-3'-phenoxybenzyl ester as a light-colored viscous oil; $n_D^{30} = 1.5528$.

EXAMPLE 62

The procedure described in Example 1 is repeated using α-(4-chlorophenoxy)-isovaleric acid as the acid component and α-allyl-3-phenoxybenzyl alcohol as the alcohol component. There is obtained α-(4-chlorophenoxy)-isovaleric acid α'-allyl-3'-phenoxybenzyl ester as a light-colored viscous oil; $n_D^{30} = 1.5597$.

EXAMPLE 63

The procedure described in Example 1 is repeated using α-vinyl-3-phenoxybenzyl alcohol as the alcohol component. There is obtained α-(4-tolyloxy)-isovaleric acid α'-vinyl-3'-phenoxybenzyl ester as a light-colored viscous oil; $n_D^{30} = 1.5562$.

EXAMPLE 64

The procedure described in Example 1 is repeated using α-(4-chlorophenoxy)-isovaleric acid as the acid component and α-vinyl-3-phenoxybenzyl alcohol as the alcohol component. There is obtained α-(4-chlorophenoxy)-isovaleric acid α'-vinyl-3'-phenoxybenzyl ester as a light-colored viscous oil; $n_D^{30} = 1.5637$.

EXAMPLE 65

The procedure described in Example 1 is repeated using α-isopropyl-3-phenoxybenzyl alcohol as the alcohol component. There is obtained α-(4-tolyloxy)-isovaleric acid α'-isopropyl-3'-phenoxybenzyl ester as a light-colored viscous oil; $n_D^{30} = 1.5462$.

EXAMPLE 66

The procedure described in Example 1 is repeated using α-(4-chlorophenoxy)-isovaleric acid as the acid component and α-isopropyl-3-phenoxybenzyl alcohol as the alcohol component. There is obtained α-(4-chlorophenoxy)-isovaleric acid α'-isopropyl-3'-phenoxybenzyl ester as a light-colored viscous oil; $n_D^{30} = 1.5528$.

EXAMPLE 67

The procedure described in Example 1 is repeated using α-ethyl-3-phenoxybenzyl alcohol as the alcohol component. There is obtained α-(4-tolyloxy)-isovaleric acid α'-ethyl-3'-phenoxybenzyl ester as a light-colored viscous oil; $n_D^{30} = 1.5497$.

EXAMPLE 68

The procedure described in Example 1 is repeated using α-(4-chlorophenoxy)-isovaleric acid as the acid component and α-ethyl-3-phenoxybenzyl alcohol as the alcohol component. There is obtained α-(4-chlorophenoxy)-isovaleric acid α'-ethyl-3'-phenoxybenzyl ester as a light-colored viscous oil; $n_D^{30} = 1.5563$.

The following Example illustrates a typical pesticidal composition containing the substituted α-aryloxycarboxylic acid esters of formula I:

EXAMPLE 69

In order to prepare an emulsifiable concentrate, the following ingredients are mixed with one another:

| | |
|---|---|
| Substituted α-aryloxycarboxylic acid ester of formula I | 500 g. |
| Condensation product of an alkylphenol and ethylene oxide; calcium dodecyl benzene sulphonate | 100 g. |
| Epoxidized soya oil having an oxirane oxygen content of about 6% | 25 g. |
| Butylated hydroxytoluene | 10 g. |

This mixture is made up to 1 liter with xylene.

I claim:

1. A substituted α-aryloxycarboxylic acid ester of the formula

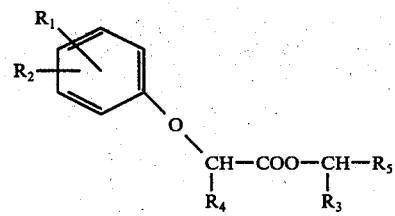

wherein $R_1$ and $R_2$ are hydrogen, halogen, alkyl containing from 1 to 3 carbon atoms, lower alkoxy, lower alkylthio, cyano or nitro; or $R_2$ and $R_1$ together are methylenedioxy; $R_3$ is hydrogen atom or cyano, lower alkenyl, lower alkynyl or lower alkyl; $R_4$ is lower alkyl group and $R_5$ is

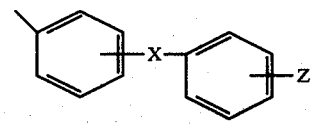

in which X is oxygen or sulphur or methylene and Z is hydrogen or fluorine.

2. A compound of claim 1 having the formula

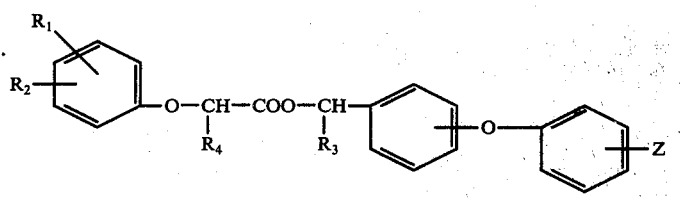

wherein $R_1$ and $R_2$ are hydrogen, halogen, alkyl containing from 1 to 3 carbon atoms, lower alkoxy, lower alkythio, cyano or nitro; or $R_1$ and $R_2$ together are methylenedioxy; $R_3$ is hydrogen atom or cyano, lower alkenyl, lower alkynyl or lower alkyl; $R_4$ is lower alkyl group and Z is hydrogen or fluorine.

3. A compound of claim 2 wherein Z is fluorine.
4. A compound of claim 2 wherein Z is hydrogen.
5. A compound of claim 1 having the formula

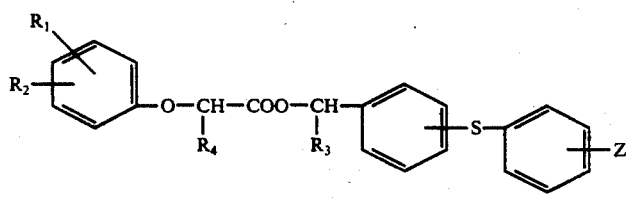

wherein $R_1$ and $R_2$ are hydrogen, halogen, alkyl containing from 1 to 3 carbon atoms, lower alkoxy, lower alkylthio, cyano or nitro; or $R_1$ and $R_2$ together are methylenedioxy; $R_3$ is hydrogen atom or cyano, lower alkenyl, lower alkynyl or lower alkyl; $R_4$ is lower alkyl group and Z is hydrogen or fluorine.

6. A compound of claim 5 wherein Z is fluorine.

7. A compound of claim 5 wherein Z is hydrogen.

8. The compound of claim 4 which is α-(4-tolyloxy)-isovaleric acid 3'-phenoxybenzyl ester.

9. The compound of claim 4 which is α-(4-chlorophenoxy)-isovaleric acid 3'-phenoxybenzyl ester.

10. The compound of claim 4 which is α-(4-ethoxyphenoxy)-isovaleric acid 3'-phenoxybenzyl ester.

11. An insecticidal composition comprising as an essential ingredient an insecticidally effective amount of a compound of the formula

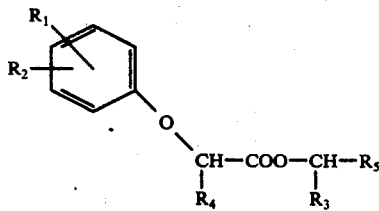

wherein $R_1$ and $R_2$ are hydrogen, halogen, alkyl containing from 1 to 3 carbon atoms, lower alkoxy, lower alkylthio, cyano or nitro; or $R_1$ and $R_2$ together are methylenedioxy; $R_3$ is hydrogen atom or cyano, lower alkenyl, lower alkynyl or lower alkyl; $R_4$ is lower alkyl group and $R_5$ is

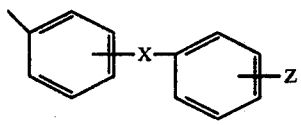

in which X is oxygen or sulphur or methylene and Z is hydrogen or fluorine and an inert carrier.

12. The composition of claim 11 wherein said compound is α-(4-tolyloxy)-isovaleric acid 3'-phenoxybenzyl ester.

13. A method of combatting insects which comprises treating the material to be protected with a compound of the formula

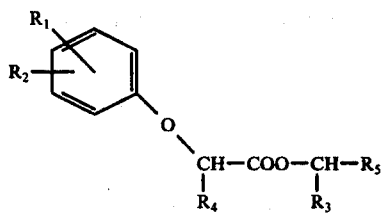

wherein $R_1$ and $R_2$ are hydrogen, halogen, alkyl containing from 1 to 3 carbon atoms, lower alkoxy, lower alkylthio, cyano or nitro; or $R_1$ and $R_2$ together are methylenedioxy; $R_3$ is hydrogen atom or cyano, lower alkenyl, lower alkynyl or lower alkyl; $R_4$ is lower alkyl group and $R_5$ is

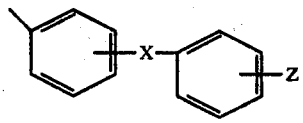

in which X is oxygen or sulphur or methylene and Z is hydrogen or fluorine.

* * * * *